United States Patent
Kusakabe et al.

(10) Patent No.: US 6,190,910 B1
(45) Date of Patent: Feb. 20, 2001

(54) MOUSE EMBRYONIC STEM CELL LINES

(75) Inventors: Moriaki Kusakabe, Ibaragi; Toshio Kamon, Tokyo, both of (JP)

(73) Assignee: The Institute of Physical and Chemical Research, Saitama (JP)

( * ) Notice: Under 35 U.S.C. 154(b), the term of this patent shall be extended for 0 days.

(21) Appl. No.: 09/439,284

(22) Filed: Nov. 15, 1999

Related U.S. Application Data

(63) Continuation-in-part of application No. 08/859,290, filed on May 20, 1997, now Pat. No. 5,985,659.

(30) Foreign Application Priority Data

May 21, 1996 (JP) ..................................................... 8-125533

(51) Int. Cl.$^7$ ................................ C12N 5/00; C12N 5/06
(52) U.S. Cl. ......................... 435/354; 435/325; 435/352; 424/582
(58) Field of Search .................... 435/325, 352, 435/354; 424/582

(56) References Cited

U.S. PATENT DOCUMENTS

| | | | | |
|---|---|---|---|---|
| 5,552,287 | * | 9/1996 | Kusakabe et al. | 435/7.4 |
| 5,985,659 | * | 11/1999 | Kusakabe et al. | 435/354 |

OTHER PUBLICATIONS

Baribault et al., Mol. Biol. Med., 6:481–492, 1989.*

H. Suemori et al., "Establishment of the Embryo–derived Stem (ES) Cell Lines from Mouse Blastocysts: Effects of the Feeder Cell Layer", Develop. Growth and Differ., vol. 29, No. 2, pp. 133–139 (1987).

M. Roach et al., "A New Embryonic Stem Cell Line from DBA/1laacJ Mice Allows Genetic Modification in a Murine Model of Human Inflammation", Experimental Cell Research, vol. 221, pp. 520–525 (1995).

E. Kawase et al., "Strain Difference in Establishment of Mouse Embryonic Stem (ES) Cell Lines", Int. J. Dev. Biol., vol. 38, pp. 385–390 (1994).

N. Noben–Trauth et al., "Efficient Targeting of the IL–4 Gene in a BALB/c Embryonic Stem Cell Line", Transgenic Research, vol. 5, pp. 487–491 (1996).

H. Kitani et al., "Isolation of a Germline–Transmissible Embryonic Stem (ES) Cell Line from C3H/He Mice", Zoological Science, vol. 13, pp. 865–871 (1996).

B. Ledermann et al., "Establishment of a Germ–Line Competent C57BL/6 Embryonic Stem Cell Line" Experimental Cell Research, 197, 254–258 (1991).

G. H. Lee et al. "Strain Specific Sensitivity to Diethylnitrosamine–induced Carcinogenesis is Maintained in Hepatocytes of C3H/HeN<<C57BL/6N Chimeric Mice" Cancer Research 51, 3257–3260 (1991).

* cited by examiner

*Primary Examiner*—John L. Leguyader
*Assistant Examiner*—Janet H. Kerr
(74) *Attorney, Agent, or Firm*—Wenderoth Lind & Ponack, L.L.P.

(57) ABSTRACT

Embryonic stem cell lines C-6 and C-2, Cr/A-3, DB1, and B6-26 have been derived from the inbred mice strains C3H/HeN, BALB/c, DBA/1J, and C57BL/6N, respectively. The embryonic stem cells are alkaline phosphatase positive and express a C3H specific antigen. The embryonic stem cell lines are useful in genetic research and the production of knockout mice.

2 Claims, No Drawings

MOUSE EMBRYONIC STEM CELL LINES

This application is a Continuation-In-Part application of U.S. application Ser. No. 08/859,290, filed May 20, 1997, now U.S. Pat. No. 5,985,659, the teachings of which are now incorporated by reference.

BACKGROUND OF THE INVENTION

1. Field of the Invention

The present invention relates to novel embryonic stem cells derived from mice.

2. Description of the Related Art

Embryonic stem cells, sometimes referred to as ES cells, are derived from inner cell mass (ICM) of fertilized eggs in blastocyst phase, and can be cultured and maintained in vitro while being kept in an undifferentiated state. Embryonic stem cells are extremely useful biological materials for preparing transgenic animals. For example, a gene knockout mouse in which a specific gene is inactivated can be produced by replacing an active gene in an embryonic stem cell chromosome with an inactivated gene by means of a homologous recombination system.

Embryonic stem cells derived from mice, hamsters, and pigs were previously reported. However, processes for establishing embryonic stem cells have not been sufficiently developed, and the sorts of embryonic stem cells are undesirably limited compared to the numbers of mouse strains that have been developed for wide variety of numerous purposes. Currently, researchers most widely use the cells derived from mouse strain 129/Sv as embryonic stem cells. However, the mice of 129/Sv are not always sufficiently bred, and accordingly, if a gene knockout mouse is established, the mouse must be disadvantageously made into a hybrid by crossbreeding with other strains. There is also a problem that the origin of embryonic stem cells established from the strain 129/Sv cannot be completely specified from a genetic viewpoint, since various kinds of substrains are involved in the strain.

Function of a certain gene is generally influenced by other genetic backgrounds in a whole-body level. Accordingly, for close comparative researches by means of gene knockout mice, it is indeed ideal to establish embryonic stem cells from an inbred mouse strain, whose basic data has sufficiently been accumulated, and compare the influence of the knockout of a gene of interest with results obtained from original strain. For these reasons, it has been desired to establish novel embryonic stem cells from inbred mouse strains. However, this class of embryonic stem cells has not been reported yet. As embryonic stem cells derived from mouse strains, embryonic undifferentiated cells disclosed in Japanese Patent Unexamined Publication (KOKAI) No. (Hei) 5-328878/1993 and the like are known. However, these cells are characterized as embryonic stem cells derived from F1 hybrid, and are not those established from inbred strains.

Accordingly, an object of the present invention is to provide novel embryonic stem cells. More specifically, the object of the present invention is to provide embryonic stem cell established from inbred mouse strains.

SUMMARY OF THE INVENTION

The inventors of the present invention conducted various studies to achieve the foregoing object, and as a result, they succeeded in establishing novel embryonic stem cells from inbred mouse strains such as C3H/HeN.

The present invention thus provide embryonic stem cells derived from mouse strains C3H/HeN, C57BL6N, DBA/1J, and BALB/c.

DESCRIPTION OF THE PREFERRED EMBODIMENTS

The embryonic stem cell of the present invention were established from mouse inbred strains of C3H/HeN, C57BL/6N, DBA/1J, and BALB/c. Among these inbred strains, C3H/HeN, C57BL/6N, and DBA/1J are genetically complete inbred strains. As for BALB/c strain, some substrains, e.g., BALB/cA and BALB/cCr, are known; however, the substrains are genetically very close to each other. These mouse strains are widely and conventionally used and can easily be obtained.

For example, the embryonic stem cells of the present invention can be established as follows: Male and female mice of the above strains are allowed to naturally mate, and on the next day, the female mice having a vaginal plug are assigned as day zero (0) of pregnancy. Blastocysts are removed from uteri of the female mice on day three (3) of pregnancy and then cultured. After hatching, the cells are transferred on feeder cells and cultivation is continued for 2 or 3 days. The feeder cells can be prepared, for example, by treating fibroblasts of 14 day old embryos of mouse BALB/cA strain with Mitomycin C. Trophectoderm adhered onto the surface of the culture dish and spread. An inner cell mass (ICM) became rising on the sheet of trophectoderm. This rising cell mass is mechanically exfoliated by fine scalpel and dissociated into a single cell in approximately 0.25% trypsin droplets. The small cell masses are transferred on the feeder cells in a 24-well plate as the primary culture. The successive treatments include the following steps: The culture medium is changed every day, and individual colonies are separately picked up after 2 to 5 days and made into single cell masses with trypsin treatments. These dissociated cells are then placed again on the feeder cells. This procedure is repeated up to tenth subculture to allow the establishment of embryonic stem cells.

EXAMPLES

The present invention will be explained more specifically by referring to the examples. However, the scope of the present invention is not limited to these examples.

(1) Collection of Ovum

Male and female mice of respective C3H/HeN, C57BL/6N, or DBA/1J strains were allowed to naturally breed, and uteri of the mice on the 3rd pregnant day were removed and washed with M2 buffer. As for BALB/c, F1 embryos between substrains that were formed by crossbreeding of BALB/cA and BALB/cCr strains were used. Embryos were washed out from the uteri with M2 buffer using a syringe equipped with a perfusion needle (30 gage). The blastocysts with zona pellucida were washed twice with M2, and then cultured in ESM medium in an incubator under 5% $CO_2$ at 37° C. for 30 hours until the embryos hatched [a droplet of the ESM medium having a diameter of 5 mm was formed and overlaid with mineral oil (Sigma), and then preliminarily incubated in an incubator under 5% $CO_2$ at 37° C.]. The hatched blastocysts were transferred on feeder cells, which had been obtained from 14 day old embryos of BALB/cA mouse and treated with Mitomycin C (10 μg/ml in DMEM), and then cultured in ESM medium. Risings of ICM were observed in the hatched embryos after two or three days.

(2) Isolation and Unbinding of ICM

The rising ICMs were picked up by suction using a 50 μl micropipette containing a small volume of phosphate buffered saline (which do not contain $Ca^{2+}$ and $Mg^{2+}$ ions) or "PBS(−)" sucked beforehand and twice washed with PBS (−), and then transferred into a droplet of a 0.25% trypsin solution and incubated at room temperature for 1 to 1.5 minutes. Before the cell mass was unbound, a small volume of ESM was added into the trypsin droplet using a micropippete to inactivate trypsin. The cell mass was divided into appropriately small pieces in separate EMS droplets, and each of the masses was transferred on feeder cells treated with Mitomycin C (10 μg/ml in DMEM). The resulting mass was assigned to the primary culture, and the culture medium was changed every day. For the second and later subcultures, cell masses were completely unbound to obtain individual cells in ESM after the treatment of trypsin for 40 to 60 seconds, and the cells were transferred on the feeder cells in a similar manner.

(a) ESM culture medium: 400 ml of DMEM (0.012 g of potassium penicillin G; 0.02 g of streptomycin sulfate; 0.6 g of sodium bicarbonate; and 4 g of DMEM were dissolved in water at a final volume of 400 ml); 2 ml of NEAA (non-essential amino acid, ×100); 4 ml of nucleoside stock solution (3 mM adenosine; 3 mM guanosine; 3 mM uridine; 3 mM cytidine; and 1 mM thymidine); 0.4 ml of 2-mercaptoethanol stock solution (5 ml of DMEM and 35 μl of 2-mercaptoethanol); 50 μl of LIF (leukemia inhibiting factor); 1.85 g of glucose; and 100 ml of FCS were mixed.

(b) 0.25% trypsin solution: trypsin (0.25 g); EDTA.2Na (0.037 g); and 1×phosphate buffered saline (−) (100 ml).

(c) M2 buffer: 15.0 ml of stock solution A (11.068 g of NaCl; 0.712 g of KCl; 0.324 g of $KH_2PO_4$; 0.586 g of $MgSO_4.7H_2O$; 8.698 ml of sodium lactate (60% syrup); 2.000 g of glucose; 0.120 g of potassium penicillin G; and 0.100 g of streptomycin sulfate in 200 ml); 2.4 ml of stock solution B (1.051 g of $NaHCO_3$ and 0.005 g of phenol red in 50 ml); 1.5 ml of stock solution C (0.036 g of sodium pyruvate in 10 ml); 1.5 ml of stock solution D (1.260 g of $CaCl_2.2H_2O$ in 50 ml); 12.6 ml of stock solution E (5.958 g of HEPES and 0.010 g of phenol red in 100 ml; adjusted to pH 7.4 with NaOH); and 600 mg of BSA were mixed and adjusted to 150 ml with distilled water.

(3) Selection of Embryonic Stem Cells

After 2 to 5-day cultivation, cell populations of various shapes were observed. Among them, flat colonies formed by morphologically uniform small cells were picked up as embryonic stem cell populations, and the colonies were treated with trypsin for 40 to 60 seconds and then subcultured on feeder cells freshly prepared as described in the above section (2). Subcultures were repeated up to tenth subculture to establish embryonic stem cells of the present invention. The cells were deposited on May 17, 1996 at the National Institute of Bioscience and Human-Technology Agency of Industrial Science and Technology (1–3, Higasi-1-chome, Tsukuba-shi, Ibaraki-ken 305 Japan) and the original depositions were transferred to the International Depositary Authority under Budapest treaty identified above on May 1, 1997.

TABLE 1

| Embryonic stem cell | Mouse strain | Accession number |
| --- | --- | --- |
| C-6 | C3H/HeN | FERM BP-5934 |
| C-2 | C3H/HeN | FERM BP-5933 |
| Cr/A-3 | BALB/c | FERM BP-5932 |
| DB1 | DBA/1J | FERM BP-5931 |
| B6-26 | C57BL/6N | FERM BP-5935 |

All of these embryonic stem cells were positive in alkaline phosphatase activity staining. In addition, among these embryonic stem cells, C-6, C-2, Cr/A-3, and DB1 were evaluated as for the ability of differentiation into germ cells by producing chimera mice according to the injection method or the aggregation method. The results are shown below.

TABLE 2

| ES cell-line[1] | Chimera mouse | Recipient embryo strain | Mating strain | Number % litter | Originate from stem cells[2] | Originate from recipient embryo[2] | Total number[2] | Ratio of ES origin (%) |
| --- | --- | --- | --- | --- | --- | --- | --- | --- |
| C-6[3] | C-6-1 | BALB/cA | BALB/cA | 3 | 27 | 0 | 27 | 100 |
| C-6[3] | C-6-2 | BALB/cA | BALB/cA | 7 | 16 | 37 | 53 | 30 |
| C-6[3] | C-6-3 | BALB/cA | BALB/cA | 9 | 16 | 44 | 60 | 27 |
| C-6[3] | C-6-4 | BALB/cA | BALB/cA | 6 | 6 | 36 | 42 | 14 |
| C-6[3] | C-6-6 | BALB/cA | BALB/cA | 6 | 48 | 0 | 48 | 100 |
| C-6[3] | CY-1 | BALB/cA | BALB/cA | 4 | 30 | 0 | 30 | 100 |
| C-2[4] | B1 | C57BL/6N | C57BL/6N | 2 | 14 | 0 | 14 | 100 |
| C-2[4] | B12 | C57BL/6N | C57BL/6N | 2 | 11 | 6 | 17 | 65 |
| C-2[4] | B13 | C57BL/6N | C57BL/6N | 1 | 2 | 2 | 4 | 50 |
| Cr-A-3[3] | CY-2 | C3H/HeN | BALB/cA | 5 | 4 | 41 | 45 | 9 |
| Cr-A-3[3] | CY-3 | C3H/HeN | BALB/cA | 2 | 0 | 15 | 15 | 0 |
| DB1[3] | DB1-1 | C57BL/6J | DBA/1J | 2 | 11[5] | 0 | 11 | 100 |

[1] Embryonic stem cells of the present invention:
 C-6 and C-2 were derived from C3H/HeN,
 CrA/3 was derived from BALB/c
 DB1 was derived from DBA/1J
[2] Number of mice
[3] Aggregation method
[4] Injection method
[5] Identified by PCR for CSA genotyping The embryonic stem cell of the present invention are derived from genetically pure inbred strains, and are therefore, extremely useful for close genetic research. For example, they are useful for the production of knockout mice and analyses of cell genealogical tree, as well as research on the mechanism of embryonic stem cell establishment. In particular, as for the embryonic stem cells derived from DBA/1J and C3H strains and the like, a chimera mouse can be prepared using a non-treated embryonic stem cell, e.g., not introduced with a gene marker, and the behavior of the cells in the tissue of the chimera mouse, that are derived from the embryonic stem cells, can be analyzed at tissue level using the monoclonal antibodies described in the U.S. Pat. No. 5,552,287, the teachings of which are now incorporated by reference.

In U.S. Pat. No. 5,552,287, a novel monoclonal antibody has been developed which specifically recognizes antigens present in mouse inbred strains consisting of DBA/1, CE/J, SM/J, IQI, PL/J, SWM/Ms, RIIIS/J, RFM/MsNrs and C3H and its congenic mouse strains thereof. By using the monoclonal antibody of U.S. Pat. No. 5,552,287 with the present ES cells derived from mouse strains DBA/1J and C3H, close genetic research, such as immunohistochemical studies (see Gang-Hong Lee et al. *"Strain Specific Sensitivity to Diethylnitrosamine-induced Carcinogenesis is Maintained in Hepatocytes of C3H/HeN⇆C57BL/6N Chimeric Mice"* Cancer Research 51, 3257–3260, Jun. 15, 1991), can be performed.

The embryonic stem cells of the present invention enables such research since the stem cells express a C3H specific antigen (CSA) recognized by the monoclonal antibody. Further, the expression of the CSA by the present ES cells are non-stage-specific in cells after cleavage divisions or in other words, at any stage throughout ontogenesis. When a chimeric mouse is generated by using the present ES cells, typically by injecting several ES cells in blastocoel cavity of blastocyst of a host mouse, the antigen CSA is expressed in all cells deriving from the ES cells in the chimeric mouse. The antigen CSA is expressed in any types of cells deriving from the ES cells, e.g., neurons, muscles, bones, liver or even in cancer cells. The antigen CSA will not affect the growth, cleavage, development, and maintenance of cells, because the antigen is inherently endogenous. In addition, cells in the chimeric mouse deriving from the ES cells can be conveniently and specifically detected by using the monoclonal antibodies.

In contrast, the prior art ES cells do not have an endogenous antigen which is expressed non-dependently in embryonic stage and whole cells in a chimeric mouse. Accordingly, when the prior known ES cells are used to generate a chimeric mouse, an exogenous marker is inevitably used to identify cells derived from the ES cells, which may affect cell development or differentiation and fail to provide reliable experimental results.

Thus, accordingly, the ES cells of the present invention can greatly contribute to the progress of embryology and developmental biology.

What is claimed is:

1. A mouse embryonic stem cell line, designated B6-26, having all of the identifying characteristics of Accession Number FERM BP-5935.

2. A mouse embryonic stem cell line, designated Cr/A-3, having all of the identifying characteristics of Accession number FERM BP-5932.

\* \* \* \* \*